(12) United States Patent
Yurino et al.

(10) Patent No.: US 6,775,621 B1
(45) Date of Patent: Aug. 10, 2004

(54) DEGREE OF HYBRIDIZATION DETECTION METHOD

(75) Inventors: Noriko Yurino, Kanagawa (JP); Kenji Yamamoto, Kanagawa (JP); Toshiaki Ito, Kanagawa (JP); Toshimasa Watanabe, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 09/459,712

(22) Filed: Dec. 13, 1999

(30) Foreign Application Priority Data

Dec. 15, 1998 (JP) .......................................... 10-355956
Nov. 18, 1999 (JP) .......................................... 11-328352

(51) Int. Cl.$^7$ ........................... G01N 33/48; C12Q 1/68
(52) U.S. Cl. ............................................. 702/19; 435/6
(58) Field of Search ............................ 702/19; 435/6; 422/50, 68

(56) References Cited

U.S. PATENT DOCUMENTS

| | | | |
|---|---|---|---|
| 5,849,486 A | | 12/1998 | Heller et al. .................... 435/6 |
| 6,023,540 A | * | 2/2000 | Walt et al. ..................... 385/12 |
| 6,197,503 B1 | | 3/2001 | Vo-Dinh et al. ................ 435/6 |

FOREIGN PATENT DOCUMENTS

| | | |
|---|---|---|
| JP | 9-512899 | 12/1994 |
| JP | 6341989 | 3/1996 |
| WO | WO 97/27329 | 1/1997 |
| WO | WO 00/34523 | 12/1999 |

OTHER PUBLICATIONS

Stephen P.A. Fodor, J. Leighton Read, Michael C. Pirrung, Lubert Stryer, Any Tsai Lu and Dennis Solas, "Light–directed, Spatially Addressable Parallel Chemical Synthesis", Research Article, Feb. 15, 1991, pp. 767–773.

Dmitry Guschin, Gennadiy Yershov, alexander Zaslavsky, Anne Gemmell, Valentin Shick, Dmitry Proudnikov, Pavel Arenkov and Andrei Mirzabekov, "Manual Manufacturing of Oligonucleotide, DNA, and Protein Microchips", Analytical Biochemistry (1997), vol. 250, pp. 203–211.

Zhen Guo, Richard A. Guilfoyle, Andrew J. Thiel, Renfeng Wang and Lloyd M. Smith, "Direct Fluorescence Analysis of Genetic Polymorphisms by Hybridization with Oligonucleotide Arrays on Glass Supports", NUCLEIC Acids Research (1994), vol. 22, No. 24, pp. 5456–5465.

Wanda G. Beattie, Lin Meng, Saralinda L. Turner, Rajender S. Carma, Dat D. Dao, and Kenneth L. Beattie, "Hybridization of DNA Targets to Glass–Tethered Oligonucleotide Probes", Molecular Biotechnology (1995), pp. 213–225.

* cited by examiner

*Primary Examiner*—Ardin H. Marschel
(74) *Attorney, Agent, or Firm*—Reed Smith LLP; Stanley P. Fisher, Esq.; Juan Carlos A. Marquez, Esq.

(57) ABSTRACT

The present invention provides a hybridization detection method capable of quantitatively determining the degree of the hybridization between a sample biopolymer and a probe biopolymer. In the method, the amount of a fluorescently labeled probe immobilized on a substrate as a spot is quantitatively determined by determining the fluorescence emitted from a fluorescent material labeling the probe, and the amount of a fluorescently labeled sample hybridized to the probe is quantitatively determined by determining the fluorescence emitted from the fluorescent material labeling the sample. The difference between the amount of the probe and the amount of the sample is normalized with the amount of the probe. Based on the normalized value, the amount of the sample hybridized to the probe can be determined relative to the amount of the probe spotted on the substrate.

12 Claims, 6 Drawing Sheets

DEGREE OF HYBRIDIZATION DETECTION METHOD

CROSS-REFERENCES TO RELATED APPLICATIONS

The present application, under 35 USC §119, claims the benefit of foreign priority applications, Japanese patent application serial number 355956/1998, filed Dec. 15, 1998 and Japanese patent application serial number 328352/1999, filed Nov. 18, 1999. These applications are explicitly incorporated herein by reference in their entirety and for all purposes.

BACKGROUND OF THE INVENTION

1. Field of the Invention

The present invention relates to a hybridization detection method for the analysis of the presence or absence of a sequence of interest in a biopolymer sample by utilizing the hybridization between the sample biopolymer and a probe biopolymer, and also relates to a biochip applicable for the method.

2. Related Background Art

Heretofore, for the detection or fractionation of a molecule in the living body, particularly the detection of DNA of interest or the detection of the presence or absence of a genomic DNA, hybridization methods have been often utilized which uses a nucleic acid or protein having a known sequence as a probe. In such hybridization methods, a sample DNA labeled with a fluorescent material is hybridized to a probe DNA immobilized onto a substrate. When the sample DNA is bound to the probe DNA, the sample DNA is in turn immobilized on the substrate together with the probe DNA. The fluorescent material attached to the sample DNA is fluorescently excited by irradiation with excitation light from a light source to emit fluorescence, and the fluorescence is then detected. In this manner, the hybridization between the sample DNA and the probe DNA can be detected.

The principle of the prior art hybridization detection method as described above is illustrated in FIGS. 7, 8 and 9.

As illustrated in FIG. 7, a given amount of probe DNA 1a is immobilized on a substrate (e.g., a glass plate) 4 as a spot 3a. Another probe DNAs 1b, 1c, . . . are also immobilized on the substrate 4 as spots 3b, 3c, . . . , respectively. In this case, however, it is impossible to immobilize all of the probe DNAs in equal amounts on the respective spots.

As illustrated in FIG. 8A, each of sample DNAs 5a, 5b, 5c, . . . is labeled with a fluorescent material 6. As illustrated in FIG. 8B, the substrate 4 spotted with the probe DNAs 5a, 5b, 5c, . . . is placed in a hybridization solution 7 and then the fluorescently labeled sample DNAs 5a, 5b, 5c, . . . are added thereto to cause the hybridization between the probe DNAs and the sample DNAs. The hybridization solution 7 is a mixed solution comprising, for example, formaldehyde, SSC (sodium chloride/trisodium citrate), SDS (sodium dodecyl sulfate), EDTA (ethylenediaminetetraacetic acid), distilled water, and the like, in which the mixing ratio between the components may vary depending on the nature of the DNAs employed.

As illustrated in FIG. 8C, if any of the sample DNAs is complementary to any of the probe DNAs, the sample DNA is hybridized to the probe DNA to form a double-stranded structure (see the illustrations for the probe DNAs 1a and 1b). If not, the sample DNA remains unbound (see the illustration for the probe DNA 1c). As illustrated in FIG. 9, the detection of the hybridization can be performed by irradiating the substrate 4 with excitation light from a lamp 9 (i.e., an excitation light source) to excite the fluorescent material 6, cutting off the light having wavelengths out of the emission wavelength range of the fluorescent material 6 with an optical filter 10, and then detecting the light emitted from each spot with a two-dimensional photosensor 8 (e.g., a CCD camera).

In this case, in the spots where the hybridization takes place (e.g., spots 3a and 3b), the fluorescent material 6 is present, and therefore fluorescent emission can be detected by exciting the fluorescent material 6 by irradiation with excitation light from the lamp 9. In contrast, in the spots where the hybridization does not take place (e.g., spot 3c), no fluorescent material 6 is present, and therefore no fluorescent emission is observed by irradiation with excitation light from the lamp 9. In this manner, a light or dark spot is observed depending on the presence or absence of the hybridization event. The image data detected by the two-dimensional photosensor 8 is transferred to a computer 13 via a controller 12 and indicated on a display.

However, in this method, upon the immobilization of probe DNAs to a substrate, it is impossible to spot all of the probe DNAs on the substrate uniformly or in equal amounts, resulting in an undesirable variation in the amount of probe DNA between the spots with a larger amount of probe DNA and the spots with a smaller amount of probe DNA. Therefore, in the detection of the hybridization, although the presence of the hybridization event between the sample DNAs and the probe DNAs can be detected, it is impossible to determine quantitatively the amount of each sample DNA hybridized to any of the probe DNAs relative to the amount of the probe DNA.

SUMMARY OF THE INVENTION

The present invention has been made for improving the above-mentioned drawbacks of the prior art methods. Accordingly, the object of the present invention is to provide a detection method which can quantitatively determine the degree of the hybridization between a probe DNA and a sample DNA.

According to the present invention, to achieve the above-mentioned object, a probe biopolymer and a sample biopolymer are labeled with different fluorescent materials, so that the probe biopolymer and the sample biopolymer present on spots deposited on a substrate can be detected separately for each spot utilizing the difference of the emission wavelength of the fluorescent materials. In the detection of the hybridization between the probe biopolymer and the sample biopolymer, the emission wavelength of the fluorescent material labeling the probe biopolymer and the emission wavelength of the fluorescent material labeling the sample biopolymer are detected separately, so that it becomes possible to separately detect and, therefore, quantitatively determine the amount of the probe biopolymer and the amount of the sample biopolymer hybridized to the probe biopolymer for each spot.

Specifically, a fluorescent material that has labeled a probe biopolymer is caused to emit fluorescence to determine the amount of the probe biopolymer immobilized on a spot deposited on a substrate (e.g., a glass plate). Another type of fluorescent material that has labeled a sample biopolymer is also caused to emit fluorescence to determine the amount of the sample biopolymer hybridized to the probe biopolymer. Then, the difference between the amount of the probe biopolymer and the amount of the sample biopolymer is normalized with the amount of the probe biopolymer. Based on the normalized value, the amount of the sample biopolymer relative to the amount of the probe biopolymer spotted on the substrate can be determined. As used herein, the term "biopolymer" refers to any polymeric material constituting a living body, such as DNA, RNA and a protein.

That is, one aspect of the present invention is a hybridization detection method for detecting the hybridization between a probe and a sample, which comprising detecting both the amount of the probe and the amount of the sample bound to the probe. As used herein, the term "probe" refers to any biopolymer to be immobilized onto a substrate, such as DNA, and the term "sample" refers to any biopolymer to be hybridized to the probe, such as DNA.

Another aspect of the present invention is a hybridization detection method for detecting the hybridization between a probe and a sample, which comprising detecting a value produced by normalizing the difference between the amount of the probe and the amount of the sample bound to the probe with the amount of the probe.

In the detection of the amounts of the probe and the sample bound to the probe, the amount of the probe may be detected prior to the hybridization, while the amount of the sample bound to the probe may be detected after the completion of the hybridization. Alternatively, both the amounts of the probe and the sample bound to the probe may be detected after the completion of the hybridization.

The detection of the amounts of the probe and the sample bound to the probe may be performed by labeling the probe and the sample with different labeling materials and then detecting the labeling materials separately.

A value produced by normalizing the difference between the amount of the probe and the amount of the sample bound to the probe with the amount of the probe may be indicated on a display.

In one embodiment of the inventive method the probe is immobilized on a support. In an even more preferred embodiment the support comprising the probe is a biochip.

Still another aspect of the present invention is a biochip comprising a fluorescently labeled probe spotted on a substrate.

The amount of the probe immobilized onto a substrate may be different for each probe and each substrate.

For easy understanding of the present invention, an example in which two biochips 1 and 2 with the same type of probe immobilized thereon and different samples A and B are used, will be described below, in which both the samples and the probes used are DNAs.

It is supposed as follows: a biochip 1 has 10 ng of a probe immobilized thereon, while a biochip 2 has 8 ng of the same type of probe immobilized thereon; the fluorescent intensities of the probe before the hybridization are 100 for the biochip 1 and 80 for the biochip 2 in terms of a 256-level gradation; and when the samples A and B are hybridized to the probe on the biochips 1 and 2, respectively, the fluorescent intensities of the samples are 70 for the biochip 1 (sample A) and 60 for the biochip 1 (sample B). From these result, it would be assessed that the DNA amount of the sample A hybridized to the probe is larger than that of the sample B hybridized to the probe. However, when compared the ratio of the DNA amount of the sample hybridized to the probe relative to the DNA amount of the probe between the samples A and B according to the method of the present invention, then it can be assessed that the sample A is actually hybridized to the probe at a lower ratio than the sample B. That is, for the samples A and B, the ratio of the DNA amount of each sample hybridized to the probe can be calculated by determining the difference between the DNA amount of the probe initially immobilized onto each biochip and the DNA amount of the sample bound to the probe and then normalizing the obtained difference with the DNA amount of the probe, as follows:

sample A: $(100-70) \div 100 = 0.3$; and sample B: $(80-60) \div 80 = 0.25$.

Accordingly, the method of the present invention enables a more precise analysis of the hybridization compared with the prior art methods in which the hybridization is analyzed only based on the fluorescent intensity of a sample after the hybridization.

This specification includes part or all of the contents as disclosed in the specifications and/or drawings of Japanese Applications Nos. 10-355956 and 11-328352, which are priority documents of the present application.

The above and other objects, effects, features and advantages of the present invention will become more apparent from the following description of embodiments thereof taken in conjunction with the accompanying drawings.

DETAILED DESCRIPTION OF THE INVENTION

The present invention will be described hereinbelow in detail by way of examples with reference to drawings. In the embodiments described below, both probe biopolymers and sample biopolymers are DNAs. However, it would be appreciated by persons skilled in the art that other biopolymers such as RNAs and proteins are also applicable in the present invention.

Figure 1B:
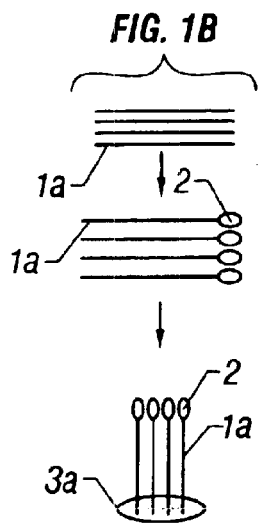
FIG. 1 illustrates the principle of an embodiment of the hybridization detection method in accordance with the present invention.
Figure 1C:
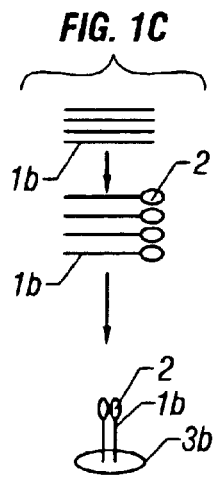
Figure 1D:
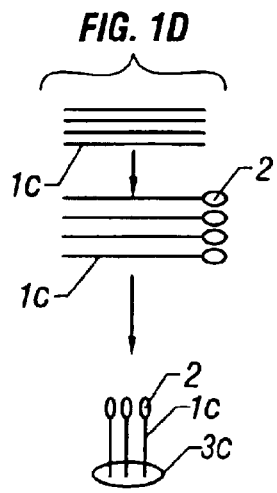
Figure 1A:
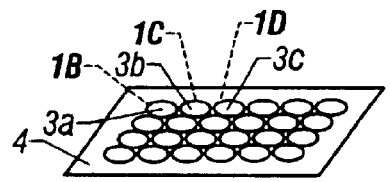
Figure 2A:
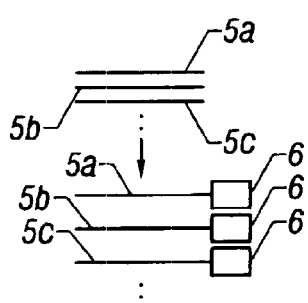
FIGS. 2A, 2B and 2C also illustrate the principle of the embodiment of the hybridization detection method in accordance with the present invention.
Figure 2B:
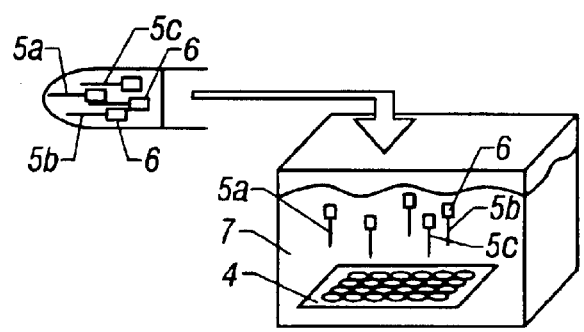
Figures 1, 2C:
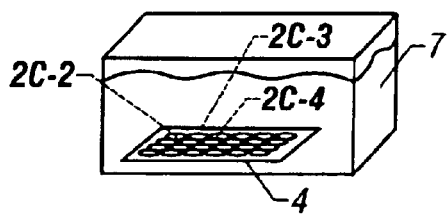
Figures 2, 2C:
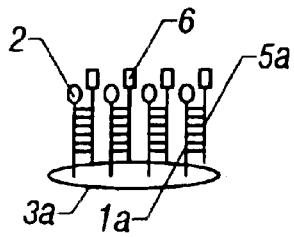
Figures 2, 2C, 3:
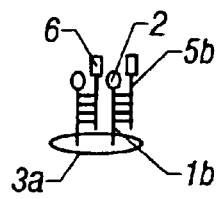
FIG. 3 also illustrates the principle of the embodiment of the hybridization detection method in accordance with the present invention.

FIGS. 1 to 3 illustrate the principle of an embodiment of the hybridization detection method in accordance with the present invention. As illustrated in FIG. 1, each of probe DNAs 1a, 1b, 1c, . . . are labeled with the same fluorescent material 2. As the fluorescent material 2, for example, fluoresce in isothiocyanate (FITC) may be used. The probe DNA 1a is immobilized onto a glass plate (substrate) 4 as a spot 3a. Other probe DNAs 1b, 1c, . . . are also immobilized onto the glass plate 4 as spot 3b, 3c, . . . , respectively.

As illustrated in FIG. 2A, each of sample DNAs 5a, 5b, 5c, . . . is labeled with another type of fluorescent material 6. As the fluorescent material 6, for example, Cy5 may be used. Upon the hybridization between the probe DNAs and the sample DNAs, as illustrated in FIG. 2B, the glass plate 4 onto which the probe DNAs are spotted (see FIG. 1) is placed in a hybridization solution 7 and the fluorescently labeled sample DNAs are added thereto. The hybridization solution 7 is a mixed solution comprising, for example, formaldehyde, SSC (sodium chloride/trisodium citrate), SDS (sodium dodecyl sulfate), EDTA (ethylenediaminetetraacetic acid) and distilled water, in which the proportion of the components may vary depending on the nature of the probe DNAs and sample DNAs employed.

If any of the sample DNAs is complementary to any of the probe DNAs, the sample DNA is hybridized to the probe DNA to form a double-stranded structure, as illustrated in FIG. 2C (see the illustrations for the sample DNAs 5a and 5b and the probe DNAs 1a and 1b). In contrast, if any of the sample DNAs is not complementary to any of the probe DNAs, the sample DNA remains unbound, as illustrated in FIG. 2C (see the illustration for the probe DNA 1c). That is, on the spots in which the hybridization takes place (e.g., spots 3a and 3b), both the fluorescent material 2 labeling the probe DNAs and the fluorescent material 6 labeling the sample DNAs individually bound to the probe DNAs are present. In contrast, on the spots in which no hybridization takes place (e.g., 3c), only the fluorescent material 2 labeling the probe DNAs is present.

The detection of the hybridization may be performed in the following manner, as illustrated in FIG. 3. The fluorescent material 6 labeling the sample DNAs, and the fluorescent material 2 labeling the probe DNAs are excited by irradiation with excitation light from a lamp 9 to emit fluorescence. The lamp 9 used as an excitation light source may be, for example, a xenon lamp having the emission wavelength range from about 300 to about 700 nm. The reason why such lamp is used is that it can cause the fluorescent emission of both FITC (excitation wavelength: 490 nm, emission wavelength: 520 nm) and Cy5 (excitation wavelength: 650 nm, emission wavelength: 667 nm). In the detection of the fluorescence, reading of emission from FITC and Cy5 is taken by using a two-dimensional photosensor 8 through an optical filter 10 having transmission wavelength of 520 nm for FITC and through another optical filter 11 having transmission wavelength of 667 nm for Cy5. The date from the two-dimensional photosensor is transferred to a computer 13 via a controller 12. The two-dimensional photosensor 8 may be, for example, a CCD camera. The optical filters 10 and 11 are movable in the direction of the arrow by driving a stage 14, and changeable to each other.

In the computer 13, the amount of each probe DNA is calculated for each spot based on the emission reading from FITC, and then the amount of the sample DNA hybridized to the probe DNA is calculated for each spot based on the emission reading from Cy5. The emission quantity Ai of FITC is reduced by the emission quantity Bi of Cy5, and the resultant difference is then divided by the emission quantity Ai of FITC, thereby providing an evaluation value Ci[Ci=(Ai−Bi)/Ai]. In this manner, the amount of a sample DNA hybridized to a probe DNA can be determined relative to the amount of the probe DNA with a high precision.

A larger Ci value [Ci=(Ai−Bi)/Ai] means that the amount of a sample DNA hybridized to a probe DNA is smaller. In contrast, a smaller Ci value means that the amount of a sample DNA hybridized to a probe DNA is larger, which also means the sample DNA has higher complementarity to the probe DNA. In the present invention, the reason why an evaluation value Ci[Ci=(Ai−Bi)/Ai] is employed for the evaluation of the ratio of hybridization is that the employment of the reduction of the amount of the sample DNA from the amount of the probe DNA makes the comparison between both the amounts more easy. This is because the amount of a probe DNA immobilized on a substrate is always larger than the amount of a sample DNA hybridized to the probe DNA in any situation.

Figures 2, 2C, 3, 4:
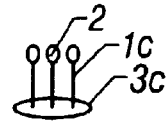
FIG. 4 is a flow chart of the processing steps for providing an evaluation value for hybridization of a sample to a probe in the hybridization detection method in accordance with the present invention.
Figure 3A:
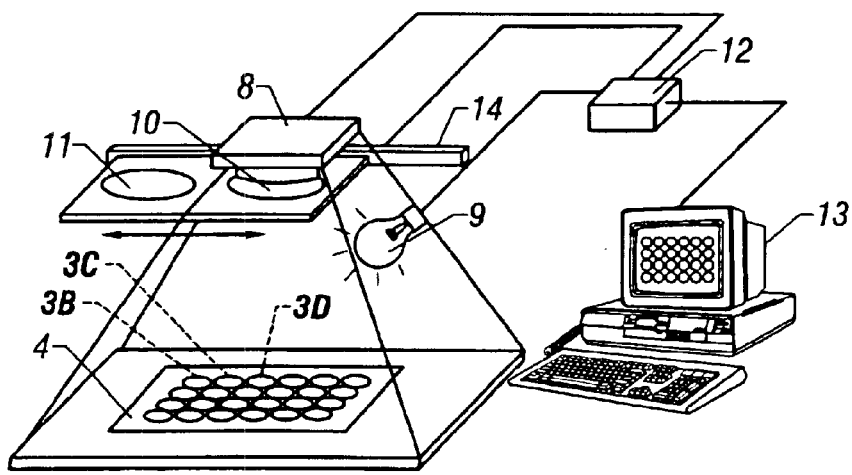
Figure 3B:
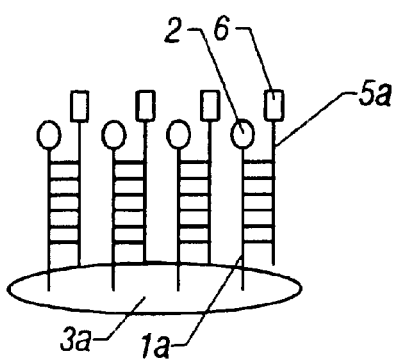
Figure 3C:
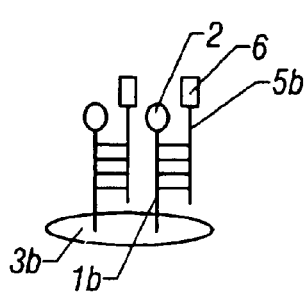
Figure 3D:
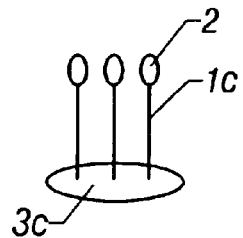
Figure 4:
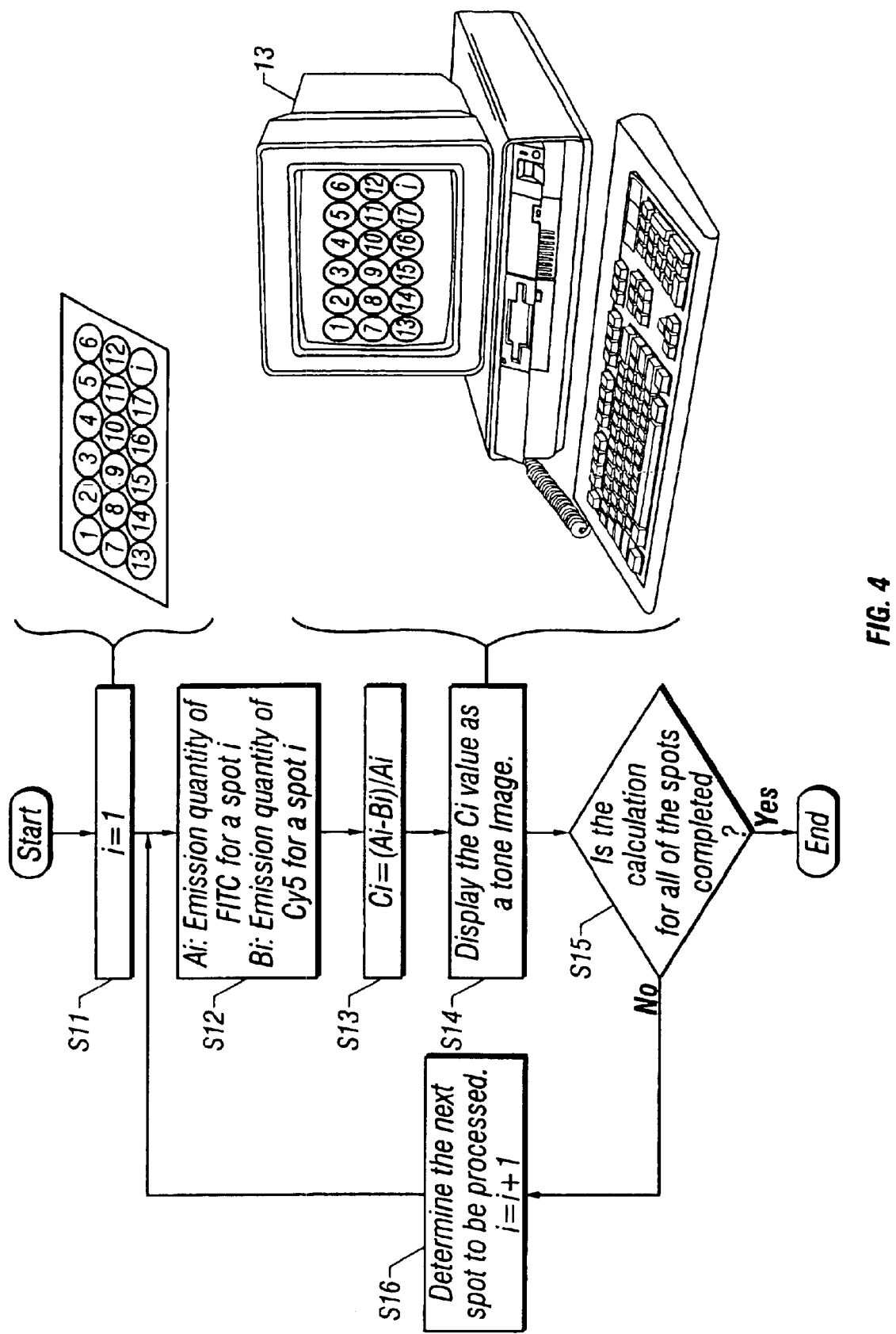

FIG. 4 is a flow chart of the processing steps for providing an evaluation value Ci. In step 11, the position number of a spot to be calculated for the evaluation value is preset. In step 12, both the emission quantity Ai of FITC and the emission quantity Bi of Cy5 are determined for a spot i. In step 13, an evaluation value Ci[Ci=(Ai−Bi)/Ai] is calculated by dividing the difference between Ai and Bi with Ai. The evaluation value Ci thus obtained represents the amount of the probe DNA not hybridized with any sample DNA. Based on the evaluation value, the degree of the complementarity between the sample DNA and the probe DNA can be assessed. In step 14, the obtained evaluation value Ci is indicated on a display of the computer 13 as a tone image. In the display, a larger Ci value is displayed brighter, while a smaller Ci value is displayed darker, or vice versa (like a positive film). In step 15, it is checked whether processing of all of the spots to be examined is completed. If not, the position number of a spot to be processed in the next step is determined in step 16, and the procedures from step 12 to step 15 are repeated. When the calculation for all of the spots to be examined is completed, the process exits.

FIGS. 5 and 6 illustrate the principle of another embodiment of the detection method in accordance with the present invention. The detection method of this embodiment includes the steps of reading an emission quantity of a fluorescent material (e.g., FITC) labeling a probe DNA, which corresponds to the amount of a probe DNA, prior to the hybridization; reading an emission quantity of another fluorescent material (e.g., Cy5) labeling a sample DNA, which corresponds to the amount of a sample DNA, after the completion of the hybridization; and then determining an evaluation value as described above.

Figure 5A:
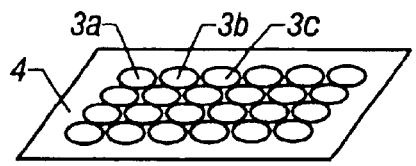
FIGS. 5A and 5B illustrate the principle of another embodiment of the hybridization detection method in accordance with the present invention.
Figure 5B:
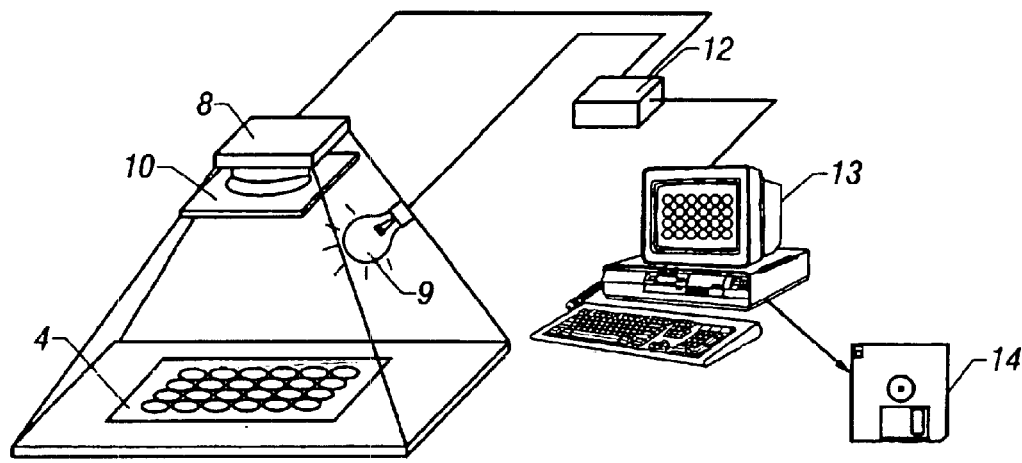

As illustrated in FIG. 5A, probe DNAs each labeled with a fluorescent material FITC are immobilized onto a glass plate (a substrate) 4 as spots 3a, 3b, 3c, . . . . The immobilization of the probe DNAs may be performed in the same manner as illustrated in FIG. 1. Prior to the hybridization, as illustrated in FIG. 5B, FITC labeling each probe DNA is exited by irradiation with excitation light to emit fluorescence, and the emission quantity of FITC is read with a two-dimensional photosensor 8, thereby determining the amount of each of the probe DNAs present for each spot. In this case, an optical filter 10 having transmission wavelength of 520 nm is located in the optical path of the photo sensor 8. The reading of the emission quantity may be performed in the same manner as illustrated for FITC in FIG. 3 above. The emission quantity Ai for each spot is stored in a storage medium 14 (e.g., a floppy disk).

Figure 6A:
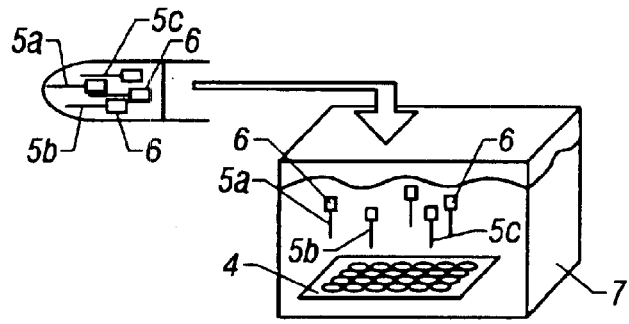
FIGS. 6A and 6B also illustrate the principle of the another embodiment of the hybridization detection method in accordance with the present invention.
Figure 6B:
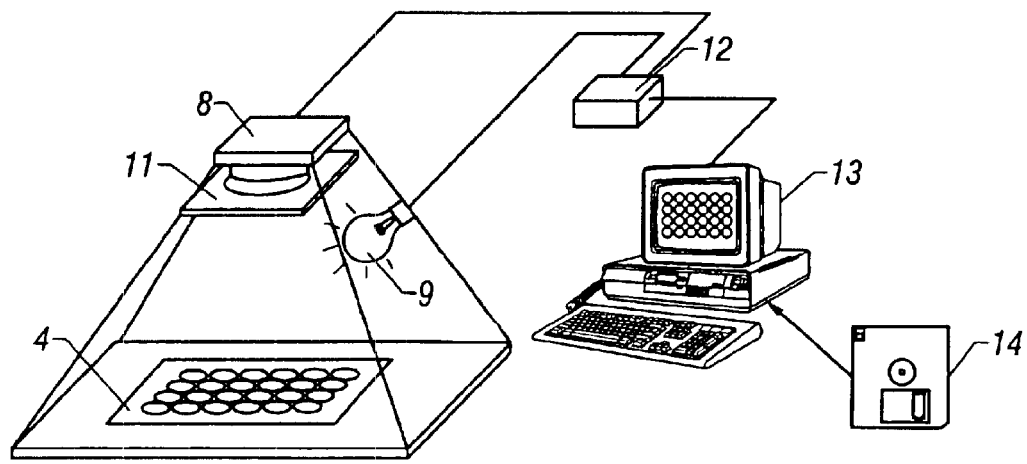
Figure 7B:
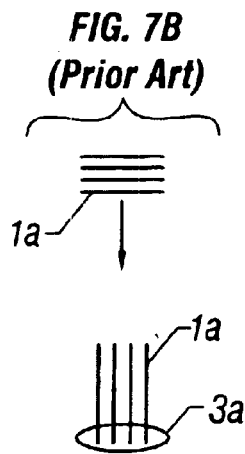
FIG. 7 illustrates the principle of an embodiment of the hybridization detection method in accordance with the prior art.
Figure 7C:
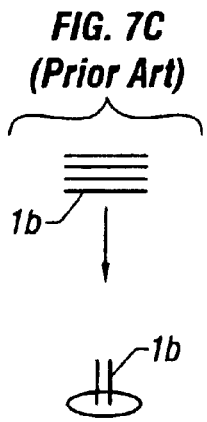
Figure 7D:
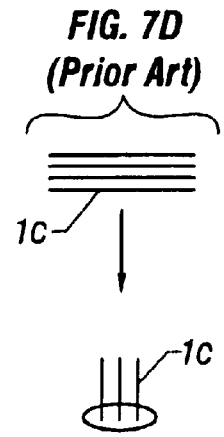
Figure 7A:
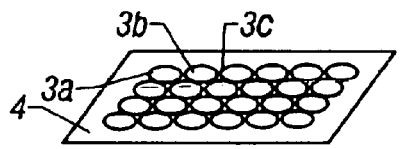
Figure 8A:
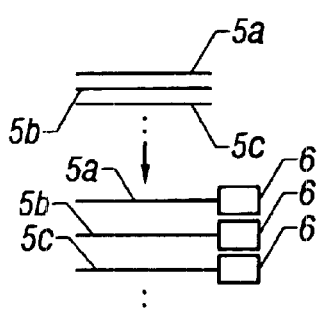
FIGS. 8A, 8B and 8C also illustrate the principle of the embodiment of the hybridization detection method in accordance with the prior art.
Figure 8B:
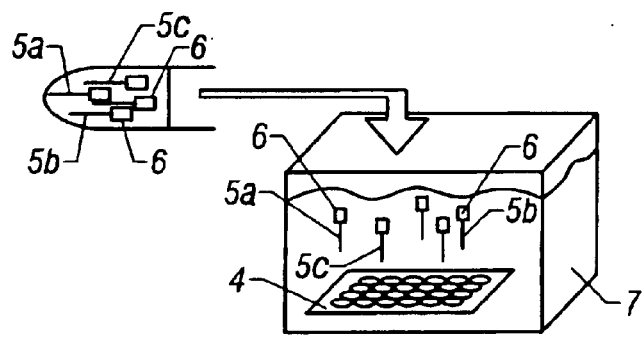
Figures 1, 8C:
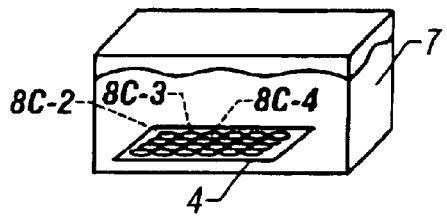
Figures 2, 8C:
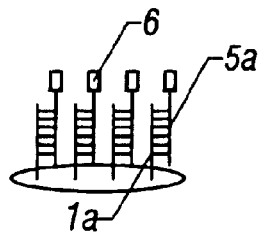
Figures 3, 8C:
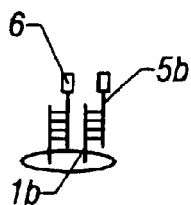
Figures 4, 8C:
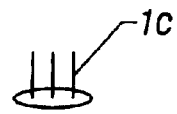
Figure 9A:
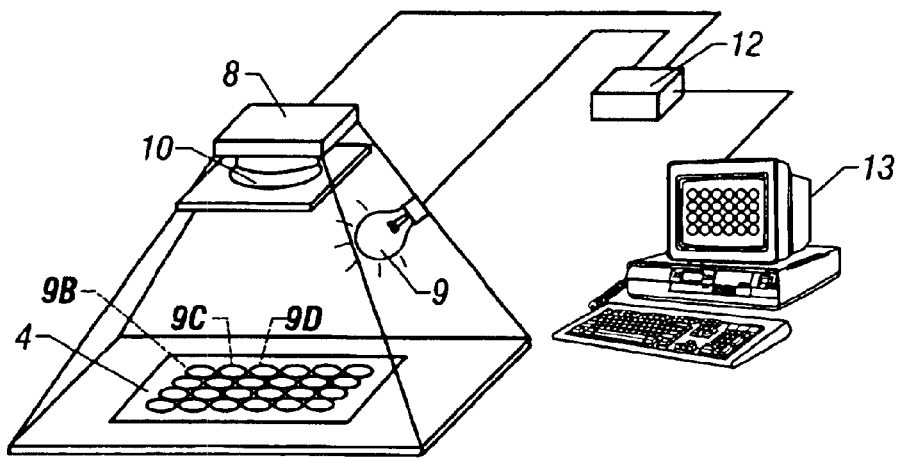
FIG. 9 also illustrates the principle of the embodiment of the hybridization detection method in accordance with the prior art.
Figure 9B:
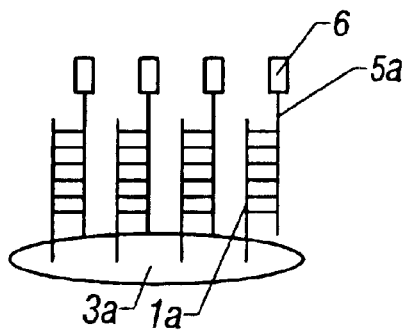
Figure 9C:
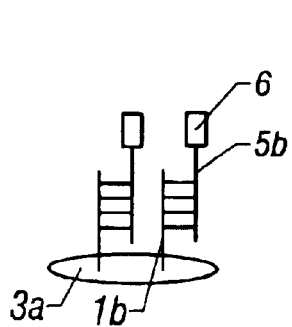
Figure 9D:
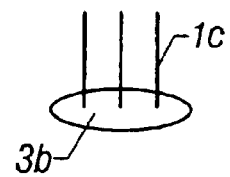

As illustrated in FIG. 6A, the hybridization between sample DNAs 5a, 5b, . . . each labeled with a fluorescent material Cy5 6 and the probe DNAs may be performed in the same manner as illustrated in FIG. 2B above. The detection of the hybridization may be performed, as illustrated in FIG. 6B, by irradiating the glass plate 4 with excitation light from the lamp 9 to cause to emit fluorescence from Cy5, and reading the emission quantity Bi of Cy5 with the two-dimensional photosensor 8. In this case, another optical filter 11 having transmission wavelength of 667 nm is located in the optical path of the photosensor 8. The reading of the emission quantity may be performed in the same manner as illustrated for Cy5 in FIG. 3 above. The emission quantity Ai of FITC stored in the storage medium 14 is then inserted into the computer 12, and the difference between the emission quantity Ai of FITC and the emission quantity Bi of Cy5 is determined. Each of the determined difference values is divided by the emission quantity Ai of FITC. The determination of the difference may be performed in the same manner as illustrated in FIG. 3 above. The method of this embodiment also enables to quantitatively determine the amounts of a sample DNA hybridized to a probe DNA.

According to the method of this embodiment, one can know what amount of a probe DNA are immobilized onto a substrate and, therefore, can also know what amount of a sample DNA is to be added for the hybridization, the location of unreactive spot(s) where any probe DNA fail to immobilize, and the like, before the hybridization is performed. Thus, the method enables to perform a hybridization experiment with a good efficiency due to its capacity to address such problems prior to the experiment.

As stated above, according to the present invention, it becomes possible to determine the amount of a probe spotted on a substrate and the amount of a sample hybridized to the probe; to calculate the precise amount of the sample hybridized to the probe (i.e., the degree of the complementarity) by determining a value produced by normalizing the difference between the amount of the probe and the amount of the sample with the amount of the probe; and therefore to determine the amount of the sample bound to the probe with a high precision.

The invention has been described in detail with reference to various embodiments, and it will now be apparent from the foregoing to those skilled in the art that changes and modifications may be made without departing from the invention in its broader aspects, and it is the invention, therefore, in the appended claims to cover all such changes and modification as fall within the true spirit of the invention.

What is claimed is:

1. A method for detecting a degree of hybridization between a plurality of types of probes and a sample comprising one type of biopolymers, the method comprising
   (a) providing a substrate on which each type of the probes is separately immobilized on each different and separate predetermined position, wherein each of the probes is labeled with a first detectable label;
   (b) providing the sample comprising the biopolymers, wherein each of the biopolymers is labeled with a second detectable label;
   (c) contacting the sample with the probes;
   (d) detecting an amount of the probes at each different and separate predetermined position of the substrate by detecting the first detectable label;
   (e) detecting an amount of the biopolymers hybridized to the probes at each different and separate predetermined position of the substrate by detecting the second detectable label; and
   (f) producing a value representing the degree of hybridization between the probes at each different and separate predetermined position and the biopolymers by dividing the difference between the amount of the probes detected at each different and separate predetermined position and the amount of the biopolymers hybridized to the probes by the amount of the probes.

2. The method of claim 1, wherein the detectable label comprises a fluorescent material.

3. The method of claim 2, wherein an emission wavelength of the fluorescent material labeling the biopolymers is detected separately from an emission wavelength of the fluorescent material labelling the probes.

4. The method of claim 1, wherein each of the biopolymers comprises a nucleic acid.

5. The method of claim 4, wherein the nucleic acid comprises a DNA or an RNA.

6. A method for detecting a degree of hybridization between a plurality of types oligonucleotide probes immobilized onto an array and one type of sample nucleic acids, the method comprising:
   (a) providing a substrate on which each type of the oligonucleotide probes is separately immobilized on each different and separate predetermined position to form an array, wherein each of the oligonucleotide probes is labeled with a first detectable label;
   (b) providing the sample nucleic acids, wherein each of the nucleic acids is labeled with a second detectable label;
   (c) contacting the sample nucleic acids with the probes;
   (d) detecting an amount of the probes at each different and separate predetermined position of the substrate by detecting the first detectable label;
   (e) detecting an amount of the sample nucleic acids hybridized to the probes at each different and separate predetermined position of the substrate by detecting the second detectable label; and
   (f) producing a value representing the degree of hybridization between the probes at each different and separate predetermined position and the sample nucleic acids by dividing the difference between the amount of the probes detected at each different and separate predetermined position and the amount of the sample nucleic acids hybridized to the probes by with the amount of the probes.

7. The method of claim 1 or claim 6, wherein the amount of the probes is detected prior to the contacting step.

8. The method of claim 1 or claim 6, wherein the amount of the biopolymers or the sample nucleic acids hybridized to the probes is detected after the completion of the contacting step.

9. The method of claim 1 or claim 6, wherein both the amount of the probes and the amount of the sample or the sample nucleic acids hybridized to the probes are detected after the completion of the contacting step.

10. The method of claim 1 or claim 6, wherein the sample nucleic acids and the probes are labeled with different labeling materials.

11. The method of claim 1 or claim 6, wherein the value is indicated on a display.

12. The method of claim 1 or claim 6, wherein the substrate comprises a biochip.

* * * * *